(12) United States Patent
Stutte et al.

(10) Patent No.: US 8,178,119 B2
(45) Date of Patent: May 15, 2012

(54) METHOD FOR THE ACARICIDAL FINISHING OF TEXTILE MATERIALS

(75) Inventors: Peter Stutte, Burgdorf (CH); Walter Bender, Rheinfelden (CH); Erich Rohrbach, Burgdorf (CH); Dominik Zimmermann, Reinach (CH)

(73) Assignee: Sanitized AG (CH)

( * ) Notice: Subject to any disclaimer, the term of this patent is extended or adjusted under 35 U.S.C. 154(b) by 764 days.

(21) Appl. No.: 11/661,495

(22) PCT Filed: Jun. 29, 2005

(86) PCT No.: PCT/EP2005/053071
§ 371 (c)(1),
(2), (4) Date: Dec. 3, 2007

(87) PCT Pub. No.: WO2006/024562
PCT Pub. Date: Mar. 9, 2006

(65) Prior Publication Data
US 2008/0260860 A1 Oct. 23, 2008

(30) Foreign Application Priority Data
Aug. 31, 2004 (CH) .................................... 1435/04

(51) Int. Cl.
*A01N 25/34* (2006.01)
(52) U.S. Cl. ........ 424/411; 424/403; 424/404; 424/405; 424/407; 424/409; 427/201; 427/421; 427/428; 427/429; 427/447; 523/122
(58) Field of Classification Search .................. None
See application file for complete search history.

(56) References Cited

U.S. PATENT DOCUMENTS

| | | | |
|---|---|---|---|
| 3,769,060 A * | 10/1973 | Ida et al. ........................ | 428/196 |
| 4,443,222 A | 4/1984 | Morris et al. | |
| 5,154,947 A | 10/1992 | Branch et al. | |
| 5,741,526 A | 4/1998 | Miyata | |
| 5,968,207 A * | 10/1999 | Li ...................................... | 8/490 |
| 6,146,651 A * | 11/2000 | Kritzler ........................ | 424/404 |

FOREIGN PATENT DOCUMENTS

| | | |
|---|---|---|
| DE | 695 10 254 | 10/1999 |
| EP | 1 468 607 A2 | 10/2004 |
| EP | 1 550 705 A1 | 7/2005 |
| JP | 2001-288014 | 10/2001 |
| JP | 2001-288017 | 10/2001 |
| JP | 2002-038380 | 6/2002 |

OTHER PUBLICATIONS

Ermolayeva et al., "Mechanism of Pyrithione-Induced Membrane Depolarization in *Neurospora crassa*," Appl. and Envir. Microbiology 61(9):3385-3390 (1995).
Gassner et al., "The Pyrethroids Permethrin and Cyhalothrin are Potent Inhibitors of the Mitochondrial Complex I," J. Pharmacology and Experimental Therapeutics 281(2):855-860 (1997).
de Saint-Georges-Gridelet, "Mise au point d'une stratégie be contrôle de l'acarien des poussières (*Dermatophagoides pteronyssinus*) par utilisation d'un fongicide," Acta Ecologica, Ecol. Applic. 2(2):117-126 (1981).
Petrova-Nikitina et al., "To the Study of Biocenotic Relationships Between House Dust Mites (Acariformes: Pyroglyphidae) and Mould Fungi," Acarina 13(1):75-84 (2005).
Van Asselt, "Interactions between Domestic Mites and Fungi," Indoor Built Enviro. 8:216-220 (1999).
Van de Maele, "A new strategy in the control of house dust mite allergy," Pharmatherapeutica 3(7):441-444 (1983).
Woodcook et al., "Fungal contamination of bedding," Allergy 61:140-142 (2006).

* cited by examiner

*Primary Examiner* — Neil Levy
(74) *Attorney, Agent, or Firm* — J.A. Lindeman & Co., PLLC

(57) ABSTRACT

The use is described of zinc pyrithione for finishing woven and non-woven textiles to render them resistant against colonization by house dust mites. Zinc pyrithione is used alone or in combination with other actives with or without other textile chemicals. The formulations comprising zinc pyrithione are applied to the textiles using the standard processes of textile finishing, such that there is a concentration of preferably 1000 to 6000 ppm of zinc pyrithione on the textile. This gives on uncoated sheetlike textiles a very distinct reduction in the mite population in testing; ideal finishes even eliminate the mite population completely.

10 Claims, No Drawings

METHOD FOR THE ACARICIDAL FINISHING OF TEXTILE MATERIALS

The present invention relates to a process for acaricidal finishing of materials, in particular of woven or non-woven textiles, such as wovens, knits and fibrous web of natural, synthetic or mixed fibers as classified in the preamble of claim 1.

Acaricidal finishing of textiles, i.e., endowing textiles with enduring protection against colonization by house dust mites, has been practiced for a long time. The active compound customarily used for this purpose is usually permethrin (CAS no. 52645-53-1), a powerful insecticide which is used for many applications, as for example in the ACTIGARD products from SANITIZED, and which belongs to the group of synthetic pyrethroids. The same effect can likewise be achieved with other pyrethroids such as deltametrin. Even natural pyrethroids, which occur in chrysanthemums, give a corresponding effect. However, these chemical species are not very stable and the durability of such finishes, if finishing can be accomplished at all, is far below that achieved through the use of synthetic pyrethroids, as for example the aforementioned permethrin, which is commercially available in various cis/trans ratios.

Neem oil, an oil of the neem tree, is also recommended for use against colonization by house dust mites. However, neem oil is too volatile for use in the OEM finishing of textiles and therefore it is on offer as a product for use in the home. Likewise too volatile for use in OEM finishing are products such as benzyl benzoate, which is said to have a synergistic effect when used together with other acaricidal products.

There are many different facts why the use of permethrin as an agent against the colonization of house dust mites on textiles is technically well established.

The textiles described above are generally finished not just against mites but also with agents which render them resistant to fungi, molds and bacteria. Zinc pyrithione is one of such agents used. It has now been found that, surprisingly, this very zinc pyrithione (CAS no.: 13463-41-7) has acaricidal properties, which was hitherto not known.

Tests were carried out where zinc pyrithione alone and zinc pyrithione in combination with other antimicrobial products, in particular with triclosan or/and 2-n-octyl-4-isothiazolin-3-one were incorporated together with permethrin in various concentrations in finishing formulations and these finishing formulations were applied to textiles consisting of natural, synthetic or mixed fibers. To compare the action against house dust mites, the same formulations were applied without permethrin. Surprisingly, textiles finished with formulations free of permethrin exhibited in the unwashed state an excellent effect against house dust mites in some cases.

It is an object of the present invention to exploit this unexpected finding and develop novel processes and agents for acaricidal and biocidal textile finishing which require little if any permethrin and for example come into consideration as an alternative to using permethrin. We have found that this object is achieved by a process according to the characterizing portion of claim 1. Preferred embodiments of the process form the subject matter of dependent claims.

The process of the present invention utilizes formulations comprising zinc pyrithione alone or in combination with other antimicrobial or acaricidal chemical species.

The present invention's use of zinc pyrithione endows zinc pyrithione finished woven or non-woven textiles, such as wovens, knits and fibrous webs, of natural, synthetic or mixed fibers with effective protection against colonization by house dust mites, such as Dermatophagoides pteronyssinus. Zinc pyrithione containing formulations are applied in post-OEM finishing alone or in combination with other textile chemicals to the textiles to be treated as will be described in detail hereinbelow.

Very interesting results on mite control were obtained with formulations comprising zinc pyrithione and used for the antimicrobial finishing of woven and non-woven textiles. Textiles finished were textiles for use as industrial textiles and home textiles such as mattress ticking, furniture covering fabrics and carpets. These are textiles which are normally not washed and are normally used under ideal conditions for development and colonization by house dust mites and therefore can be successfully colonized by mites.

Similarly interesting cuts in the mites count were obtained with formulations comprising the active chemical species triclosan and/or 2-n-octylisothiazolin-3-one. The two former active chemical species even give fairly good cuts in the number of mites without zinc pyrithione, but a reduction to zero mites was not quite achieved at the concentrations of the active chemical species as tested and as normally used for antimicrobial finishing. At higher concentrations, elimination of mites is technically possible, but not economically advantageous over the combinations of the active chemical species with permethrin. This also applies to compounds such as dimethyltetradecyl-[3-(trimethoxysilyl)propyl]ammonium chloride, didecylmethyl-[3-(trimethoxysilyl)propyl]ammonium chloride or dimethyloctadecyl-[3-(trimethoxysilyl)propyl]ammonium chloride.

Formulations comprising zinc pyrithione give an effect against house dust mites in the zinc pyrithione concentration range from 600 to 10 000 ppm, but preferably between 1000 ppm and 6000 ppm and ideally in the range from 1500 to 3000 ppm. The concentration is reported on dry weight of fabric. The optimum concentration depends crucially on the constitution of the textile to be finished and the other textile chemicals used.

When the zinc pyrithione containing formulation is applied using a classic process of post-OEM finishing of textiles, such as the padding process, the blade process, in particular in the case of coatings, the spraying or foam process, it is ideal to use formulations comprising between 5% and 60% of zinc pyrithione, but preferably comprising a concentration between 10% and 50% of zinc pyrithione. As well as zinc pyrithione, such formulations may further comprise up to 15% of triclosan. Further active chemical species can be added in the application bath, as will be appreciated. This method is particularly advisable when 2-n-octylisothiazolin-3-one is to be applied concurrently with zinc pyrithione, but also works without problems when formulations comprising 1,2-benzisothiazolin-3-one, quaternary ammonium compounds such as for example didecyldimethylammonium chloride, dimethyltetradecyl-[3-(trimethoxysilyl)propyl]ammonium chloride or dimethyloctadecyl-[3-(trimethoxysilyl)propyl]ammonium chloride or poly(hexamethylenebiguanide) hydrochloride are to be co-incorporated in the recipe.

However, when zinc pyrithione is applied from the polymer melt, by the hot melt process, for example after dispersion in a polyolefin such as polyethylene or polypropylene or best of all a copolymer such as ethylene-vinyl acetate (EVA) copolymer or in the form of a powder by the zinc omadine being mixed with a polymeric powder, as for example polyurethane, polyethylene, polypropylene or polyvinyl chloride with or without the addition to the powder of a dustproofing agent, the zinc pyrithione should be used in a concentration of 2% to 100%, preferably 3% to 35% and ideally 5% to 15% of zinc pyrithione alone or in combination with other antimicrobial actives, for example up to 15% of triclosan. This formulation must be applied to the textile to be finished such that the concentration of zinc pyrithione is in the range from 600 to 10000 ppm, but preferably between 1000 ppm and 6000 ppm and ideally in the range from 1500 to 3000 ppm. But with this process of application the best results are obtained when some permethrin is afterall admixed to the formulation, so that the amount of permethrin is between 20 and 200 ppm, based on the dry finished textile. Since some of the overall acaricidal effect is due to the permethrin, the amount of zinc pyrithione can be adjusted such that an optimum antimicrobial effect is achieved without exceeding that level.

The surprise about the action of zinc pyrithione against the colonization of textiles by house dust mites is only rivaled by the surprise about the absence of a comparable effect of zinc pyrithione in foams composed of polyurethane and in films or coatings composed of plasticized PVC. On polyurethane foams based on polyester polyol, 2000 ppm of zinc pyrithione allowed a growth in the population of mites by a factor of 1.6, which is only insignificantly less than the corresponding control sample at a factor of 2.6. In the case of plasticized PVC, even 3000 ppm of zinc pyrithione allowed a growth in the population of mites by a factor of 1.4, while the PVC control sample returned a growth of again by a factor of 2.6. Both values are insufficient for the protection of the finished articles against colonization by mites, but they do form the basis for enhancement of the protection without the complete effect having to be supplied by the other active, permethrin for example.

Testing of the effect against house dust mites was carried out in the experiments according to one of the two methods described hereinbelow:
1. The textile sample is cut to a size of 8×8 cm and placed on a glass plate of the same size. About 50 house dust mites in the adult stage, which were counted under the microscope, were placed in the center of the sample. Other stages were likewise present of course but are not counted. Some food (see method 2) is added. A 5 mm thick rubber plate with a 30 mm diameter hole in the middle is placed on the sample. The hole is covered from the top with a filter paper, and a metal plate with a hole in the middle is placed on the filter paper such that the hole is congruently positioned above the hole in the rubber plate. The sample plates thus prepared are fixed with clips and are then incubated for 6 or 8 weeks in an incubator at saturated humidity at 25° C. After the period of 6 or 8 weeks, the living adult mites were again counted under the microscope. In this method, the change in the number of mites compared with the initial value is calculated. The test is carried out in duplicate.
2. The AFNOR NF G 39-011 test method, as carried out for example by TEC Laboratory, F-64600 Anglet, again utilizes 50 adult house dust mites, Dermatophagoides pteronyssinus, per test sample, which come from a stock culture from INRA Bordeaux and were bred for several years at 76% humidity at 25° C. in the complete absence of insecticides. The mites were fed on a mixture of wheat germ and brown brewer's yeast. The test is carried out at 17 to 23° C. The test duration is six weeks, and the mites are counted after they were driven out by application of heat. The test is carried out in quadruplicate. The reduction in the number of mites after six weeks compared with a non-finished control sample is determined.

The advantages of the formulations according to the present invention are:
Formulations requiring very few different active ingredients, i.e., for example fewer active ingredients than hitherto, and nonetheless protect textiles against the entire spectrum of microorganisms and additionally against colonization by house dust mites.
Formulation without halogens and thus also without the wastewater-relevant AOX (absorbable organic halogen).
Component against house dust mites which is not volatile under thermally demanding application conditions and which therefore presents itself for application in combination with hydrophobic finishes such as fluorocarbons or resins. Applications where heat setting is required.
Minimal use concentrations of antimicrobially active substances to achieve an optimum, broad antimicrobial spectrum of action; in the case of zinc pyrithione, this is the familiar protection against bacteria, microfungi, yeasts and algae and surprisingly even against house dust mites.
Use of a very well known and toxicologically examined chemical species in such low concentrations, optimized to the stated objective, that no adverse consequences are likely for warm-blooded animals in general and humans in particular.
Use of an active chemical species which is capable of withstanding heat-setting on the textiles without chemical changes and, what is more, does not evaporate. This often is not the case with other chemical species frequently used for the same use sector. At least, this is the irresistible conclusion from analytical results on textiles after application and heat setting.

The invention will now be more particularly elucidated by means of a series of operative examples. These examples shall not restrict the invention. Percentages are mass percent on the dry weight of the fabric to be finished, unless otherwise stated.

EXAMPLE 1

1.5% of Sanitized TH 22-27, an aqueous disperse formulation comprising 15% of zinc pyrithione, is padded onto a woven cotton fabric having an areal weight of 198 g/m2. The finished fabric is dried on a tenter at 120° C. for 2 minutes and subsequently tested for its efficacy against mites by the abovementioned method 1. There were no longer any live mites on either sample after the test.

EXAMPLE 2

1.0% of Sanitized TH 21-06, an aqueous dispersion comprising 15% of zinc pyrithione and 3% of triclosan, is padded onto a woven cotton fabric having an areal weight of 198 g/m2, a woven polyester fabric having an areal weight of 180 g/m2 and a woven polyamide fabric having an areal weight of 190 g/m2. The fabrics are all dried on a tenter at 120° C. for 2 minutes and subsequently tested for their efficacy against mites by the abovementioned method 1. There were no longer any live mites on any of the samples after the test.

EXAMPLE 3

1.0% of an aqueous dispersion comprising 15% of zinc pyrithione is padded together with 3% of NUVA TTC or with 4% of NUVA HPU or with 4% of NUVA HPC, three fluorocarbons from Clariant AG, CH-4132 Muttenz, onto woven cotton fabric, woven polyester fabric or woven polyamide fabric. The fabric samples were dried at 120° C. for 2 minutes and subsequently cured at 150° C. for 90 seconds. These samples were tested for their efficacy against mites by method 1. There were no longer any live mites on any of the samples after the test.

EXAMPLE 4

1.5% of an alcoholic-aqueous dispersion comprising 10% of zinc pyrithione and 5% of 2-n-octylisothiazolin-3-one is padded onto woven cotton fabric, dried at 120° C. on a tenter for 2 minutes and tested for its efficacy against mites by method 1. There were no longer any live mites on any of the samples after the test.

EXAMPLE 5

Fabric for mattress ticking composed of a blend of cotton and polyester is finished with 1.0% or 1.2% or 1.5% of a formulation comprising 15% of zinc pyrithione together with 3% to 5% of acrylate copolymers in each case, tenter dried at 120° C. for 2 minutes and subsequently tested for efficacy against mites by method 2. All the samples finished with 1.2% or 1.5% of the formulation comprising 15% of zinc pyrithione are completely free of mites after the test. The samples finished with 1.0% of the formulation exhibit on average a mite inhibition rate (MIR) of 99.3% compared with the non-finished control fabric and thus likewise a dramatic decrease in the mite population.

EXAMPLE 6

0.4% of an aqueous formulation comprising finely disperse 48% of zinc pyrithione is padded together with a wetting agent and a nonionized surfactant onto a woven cotton fabric and dried at 180° C. for 1 minute and tested for its efficacy against mites by method 1. There were no longer any live mites on any of the samples after the test.

EXAMPLE 7

0.7% of the formulation comprising 15% of zinc pyrithione and 1.5% of Sanitized TB 83-35, of a formulation comprising 2-n-octylisothiazolin-3-one and 1,2-benzisothiazolin-3-one is padded onto cotton, dried at 120° C. for 2 minutes and tested for their efficacy against mites by method 1. There were no longer any live mites on any of the samples after the test.

EXAMPLE 8

1.1% or 2.3% of Sanitized TB 83-35, a formulation comprising 2-n-octylisothiazolin-3-one and 1,2-benzisothiazolin-3-one is padded onto cotton, dried at 120° C. for 2 minutes and tested for its efficacy against mites by method 1. The samples show a reduction in the number of live mites of 43% and 92%, respectively, compared with the initial value, whereas the number of mites on the untreated control sample has increased by a factor of 3.

EXAMPLE 9

Woven cotton fabrics were padded, from the same application bath, with 0.8% of a formulation comprising 15% of zinc pyrithione and 0.5% of Sanitized T 99-19, a formulation comprising the active chemical species dimethyltetradecyl-[3-(trimethoxysilyl)propyl]-ammonium chloride, dried at 120° C. for 2 minutes and tested for their efficacy against mites by method 1. There were no longer any live mites on any of the samples after the test.

EXAMPLE 10

Woven cotton fabrics padded with 0.56% of Sanitized T 99-19, a formulation comprising the active chemical species dimethyltetradecyl-[3-(trimethoxysilyl)propyl]ammonium chloride, dried at 120° C. for 2 minutes and tested for their efficacy against mites by method 1 (6 weeks). The samples after the test exhibit on average a reduction in the number of live mites of 34%. This reduction versus a growth rate by a factor of 5.3 for the non-finished control sample.

EXAMPLE 11

Padding is used to apply 1000 ppm of triclosan to cotton and 1400 ppm of triclosan to a furniture covering fabric of polyester. The fabrics were tenter dried at 120° C. for 2 minutes and then tested for their efficacy against mites by method 1 (6 weeks). The cotton samples after the test show on average a reduction in the number of live mites of 57%, and the polyester samples a 38% reduction. The control samples in this experiment showed a growth rate of 273%.

EXAMPLE 12

A master batch comprising 8% of zinc pyrithione in EVA was melted together with additional EVA and applied to a mattress ticking by means of the hot melt process, a process where the fabric to be finished is coated, via a roll, on one side with the molten polymer such that the fabric is rendered slip-resistant thereby. The zinc pyrithione concentration on the final fabric was 1600 ppm. This fabric was then tested for its efficacy against mites by method 1 (6 weeks). The average reduction in mite population compared with the initial value varies somewhat in the range from 30% to 80% in this method, but still constitutes a very distinct reduction compared with the non-finished control sample having a growth rate of 390% in this test series.

EXAMPLE 13

A powder comprising 24% of zinc pyrithione as well as pulverized polyethylene and a dustproofer solution based on petroleum is applied to a gray state mattress ticking fabric together with EVA. A fibrous web is placed on top and the now embedded EVA comprising the zinc pyrithione containing formulation is melted via heated rolls, pressed and cooled back down. The ticking thus produced comprises 2100 ppm of zinc pyrithione and is tested for efficacy against mites by method 1 (6 weeks). The average reduction in mite population compared with the initial value is not constant and varies in particular according to whether the mites are applied to the fibrous web or to the fabric. The reduction achieved is between 50% and 90% in the case of the fibrous web and between 30% and 70% in the case of the fabric. The control sample gave a growth rate of 460% in this test series.

EXAMPLE 14

To an initial charge of 7.25 kg of water are added 150 g of Baygard foamer (pH 6.5, amphoteric), 1.4 kg of Nuva HPS and 1.2 kg of Sanitized TB 22-27 comprising 15% of zinc pyrithione. The batch is foamed and 55 g/m2 are applied to the pile side of a carpet having a fiber weight of 400 g/m2. The carpet is tenter dried at 110° C. and tested for efficacy against mites by method 2. The average reduction in mite population compared with the initial value is not constant and amounts to 58% on average. The control sample gave a growth rate of 760% in this test series.

The invention claimed is:

1. A process for finishing a woven or non-woven textile to render it resistant against colonization by mites, comprising the step of applying a formulation comprising zinc pyrithione and an antimicrobial active agent selected from the group consisting of triclosan, 2-n-octylisothiazolin-3-one, 1,2-benzisothiazolin-3-one, didecyldimethylammonium chloride, dimethyltetradecyl-[3-(trimethoxysilyl) propyl]ammonium chloride, didecylmethy-[3-(trimethoxysilyl)propyl]ammonium chloride, dimethyloctadecyl-[3-(trimethoxysilyl)propyl]ammonium chloride, poly(hexamethylenebiguanide) hydrochloride, and mixtures thereof to said textile,
   wherein the formulation comprises 2 wt % to 60 wt % zinc pyrithione, 3 wt % to 15 wt % antimicrobial active agent, a polymeric binder, and a hydrophobicizinq agent;
   wherein the textile is a furniture covering fabric or mattress ticking;
   wherein the formulation is applied by a padding process, a blade process, a spraying process, or a foam coating process, or as a powder or from a polymer melt; and
   wherein the concentration of zinc pyrithione, based on the dry finished textile, is between 600 and 10,000 ppm.

2. A process according to claim 1, wherein the formulation comprising zinc pyrithione and the antimicrobial active agent optionally comprises another antimicrobial active agent or a textile chemical and is applied to the textile such that the applied concentration of zinc pyrithione, based on dry fabric weight of the textile to be finished, is between 600 and 10,000 ppm.

3. A process according to claim 2, wherein the applied concentration of zinc pyrithione, based on dry fabric weight of the textile to be finished, is between 1000 ppm and 6000 ppm.

4. A process according to claim 3, wherein the applied concentration of zinc pyrithione, based on dry fabric weight of the textile to be finished, is between 1500 and 3000 ppm.

5. A process according to claim 1, wherein the formulation comprises 10 wt % to 50 wt % zinc pyrithione.

6. A process according to claim 5, wherein the formulation comprises 10 wt % to 30 wt % zinc pyrithione.

7. A process according to claim 1, wherein:
   the formulation comprises 10 wt % to 50 wt % zinc pyrithione, 3 wt % to 15 wt % triclosan, and the hydrophobicizing agent is a fluorocarbon hydrophobicizing agent;
   the formulation is applied by padding or a blade coating process; and
   the concentration of zinc pyrithione, based on the dry finished textile, is between 1,000 and 6,000 ppm.

8. A process according to claim 7, wherein:
   the formulation comprises 10 wt % to 30 wt % zinc pyrithione and 3 wt % to 15 wt % triclosan; and
   the concentration of zinc pyrithione, based on the dry finished textile, is between 1,500 and 3,000 ppm.

9. A process according to claim 1, wherein:
   the formulation comprises 3 wt % to 35 wt % zinc pyrithione; and
   the concentration of zinc pyrithione, based on the dry finished textile, is between 1,000 and 6,000 ppm.

10. A process according to claim 9, wherein:
    the formulation comprises 5 wt % to 15 wt % zinc pyrithione and 3 wt % to 15 wt % triclosan; and
    the concentration of zinc pyrithione, based on the dry finished textile, is between 1,500 and 3,000 ppm.

* * * * *